United States Patent
Woodward et al.

(10) Patent No.: US 6,719,447 B1
(45) Date of Patent: Apr. 13, 2004

(54) VERSATILE OPERATORY LIGHT SYSTEM

(75) Inventors: Gary W. Woodward, Battle Ground, WA (US); Brad B. Heckerman, Florence, MT (US); Dennis A. Meuchel, Missoula, MT (US)

(73) Assignee: Micron Dental Manufacturing, Inc., Missoula, MT (US)

( * ) Notice: Subject to any disclaimer, the term of this patent is extended or adjusted under 35 U.S.C. 154(b) by 1089 days.

(21) Appl. No.: 09/092,577

(22) Filed: Jun. 5, 1998

Related U.S. Application Data

(63) Continuation-in-part of application No. 08/401,717, filed on Mar. 10, 1995, now Pat. No. 5,775,896.

(51) Int. Cl.$^7$ .......................................... F21W 131/202
(52) U.S. Cl. ........................ 362/573; 362/572; 362/558; 362/554; 362/580; 362/577; 385/117
(58) Field of Search .................................. 362/554, 558, 362/572, 573, 574, 577, 581, 580, 373, 294; 385/116, 117, 118

(56) References Cited

U.S. PATENT DOCUMENTS

| | | | | |
|---|---|---|---|---|
| 3,131,690 A | * | 5/1964 | Innis et al. | 362/574 X |
| 4,579,419 A | * | 4/1986 | Scrivo | 362/573 X |
| 4,900,122 A | * | 2/1990 | Frank et al. | 385/117 X |
| 5,099,399 A | * | 3/1992 | Miller et al. | 362/580 |
| 5,634,711 A | * | 6/1997 | Kennedy et al. | 362/572 X |
| 5,930,424 A | * | 7/1999 | Heimberger et al. | 362/554 X |

* cited by examiner

*Primary Examiner*—Laura K. Tso
(74) *Attorney, Agent, or Firm*—TraskBritt

(57) ABSTRACT

A low voltage power supply includes a plurality of output terminal pairs interconnected by electrical circuitry effective to permit individual adjustment of the voltages applied between each such pair for powering simultaneously a plurality of light sources at individually selected voltages. The light sources are associated with dental handpieces through umbilical tubings, an exemplary one of which includes a bundle of flexible, light-conducting fibers connected between a first coupling fixture holding a subminiature bulb and a second coupling structurally adapted for connection to a dental handpiece.

17 Claims, 11 Drawing Sheets

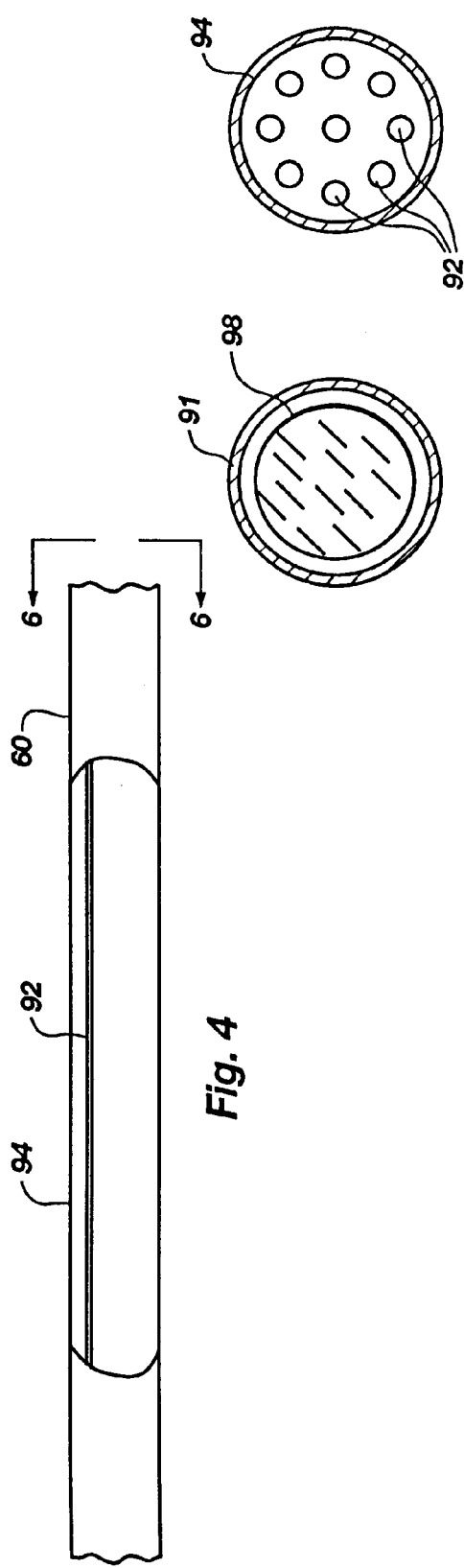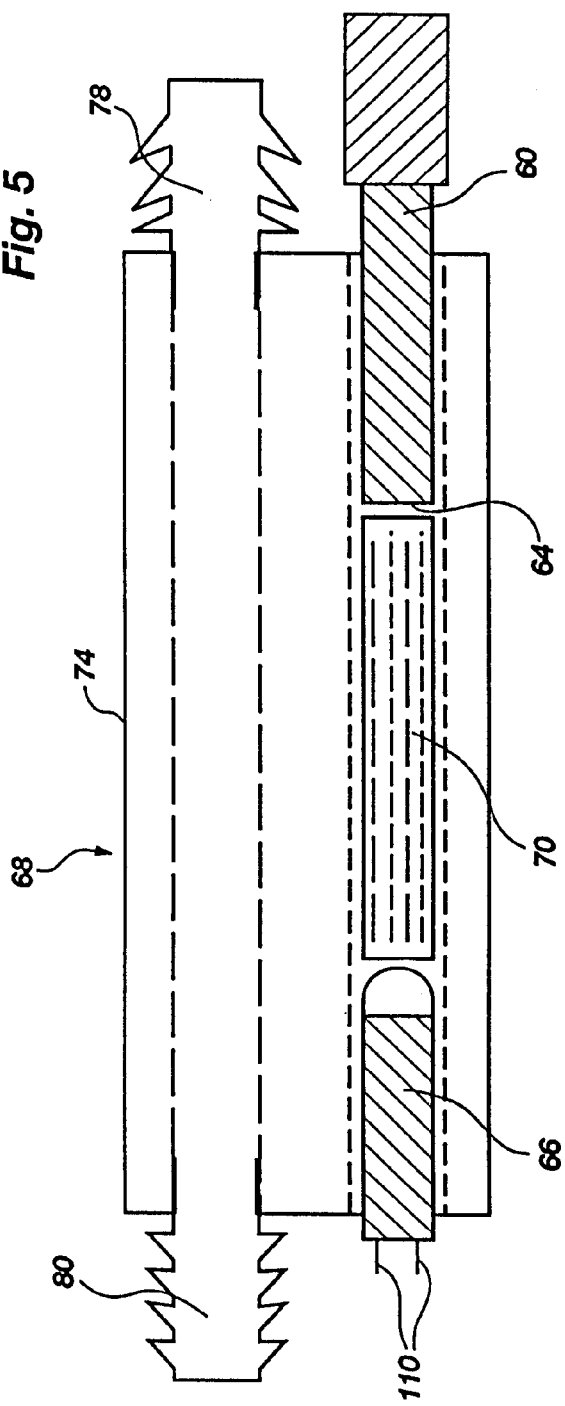

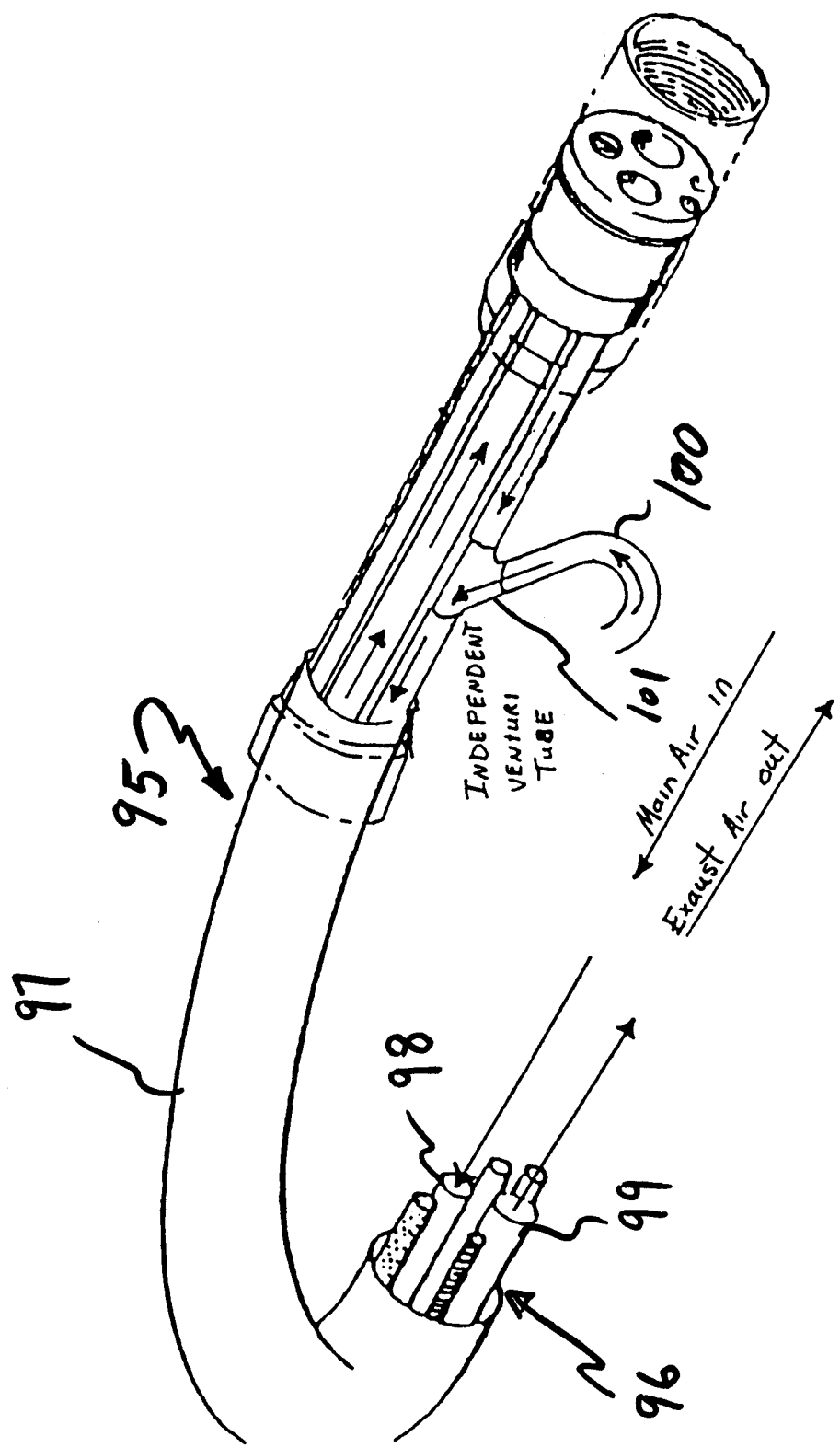

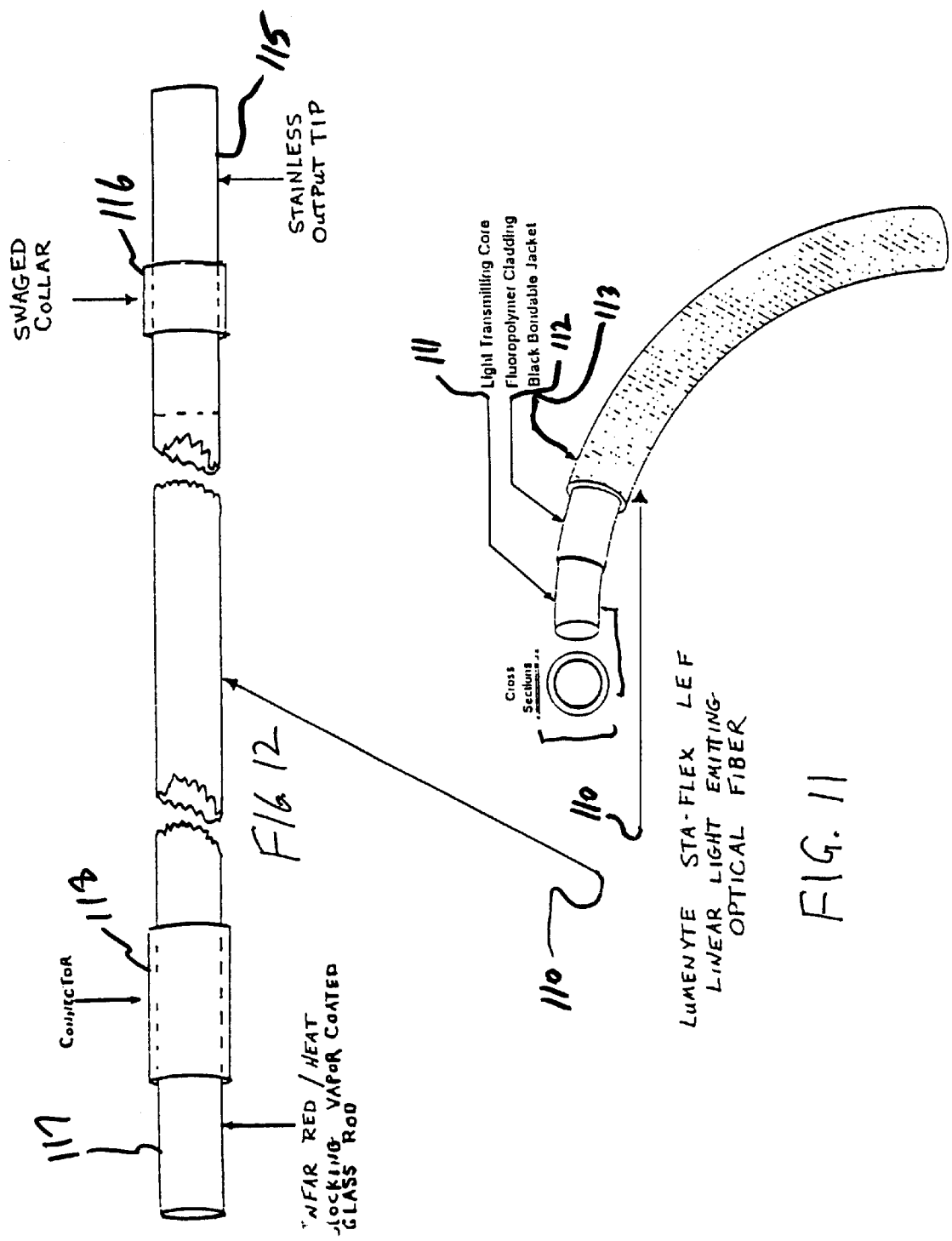

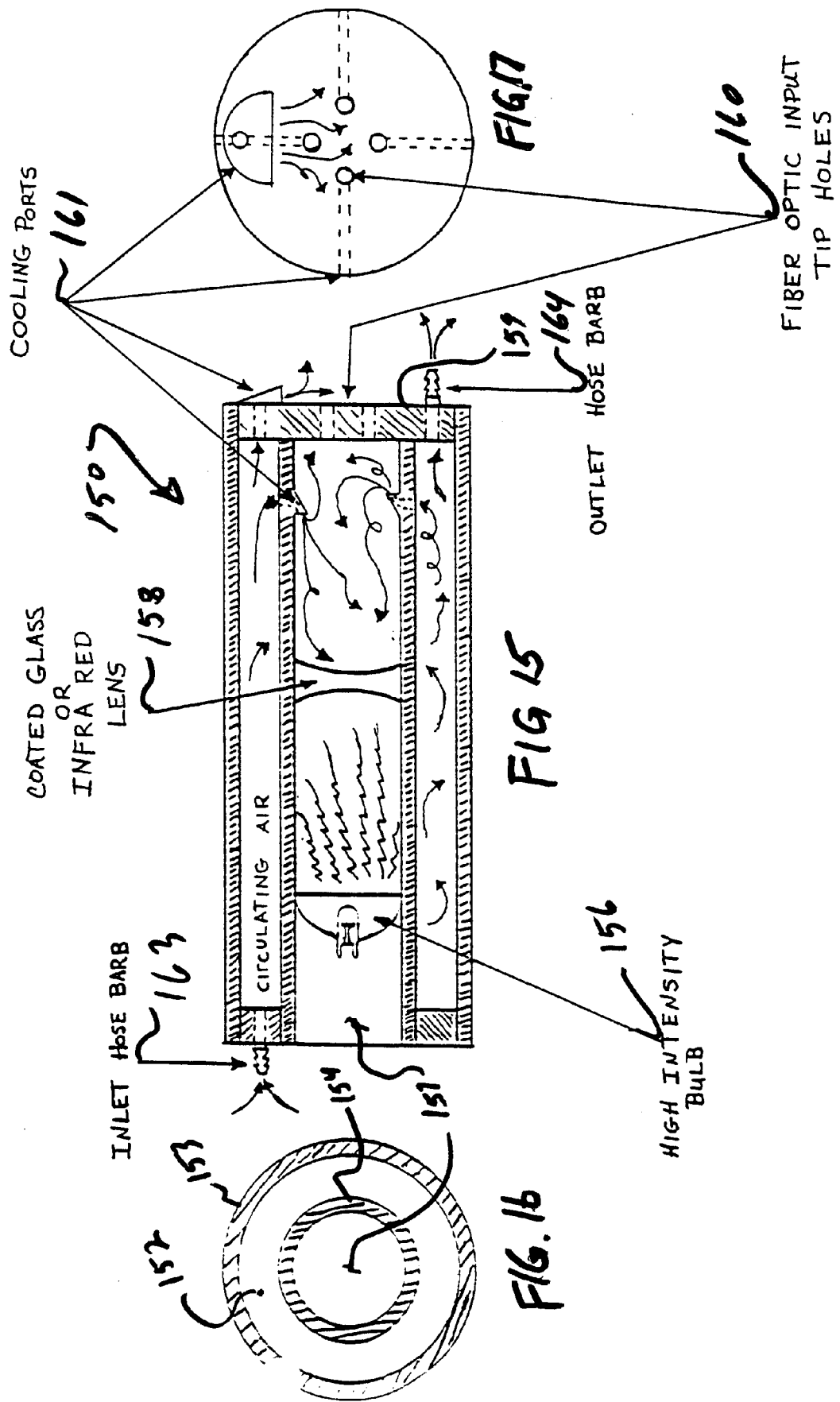

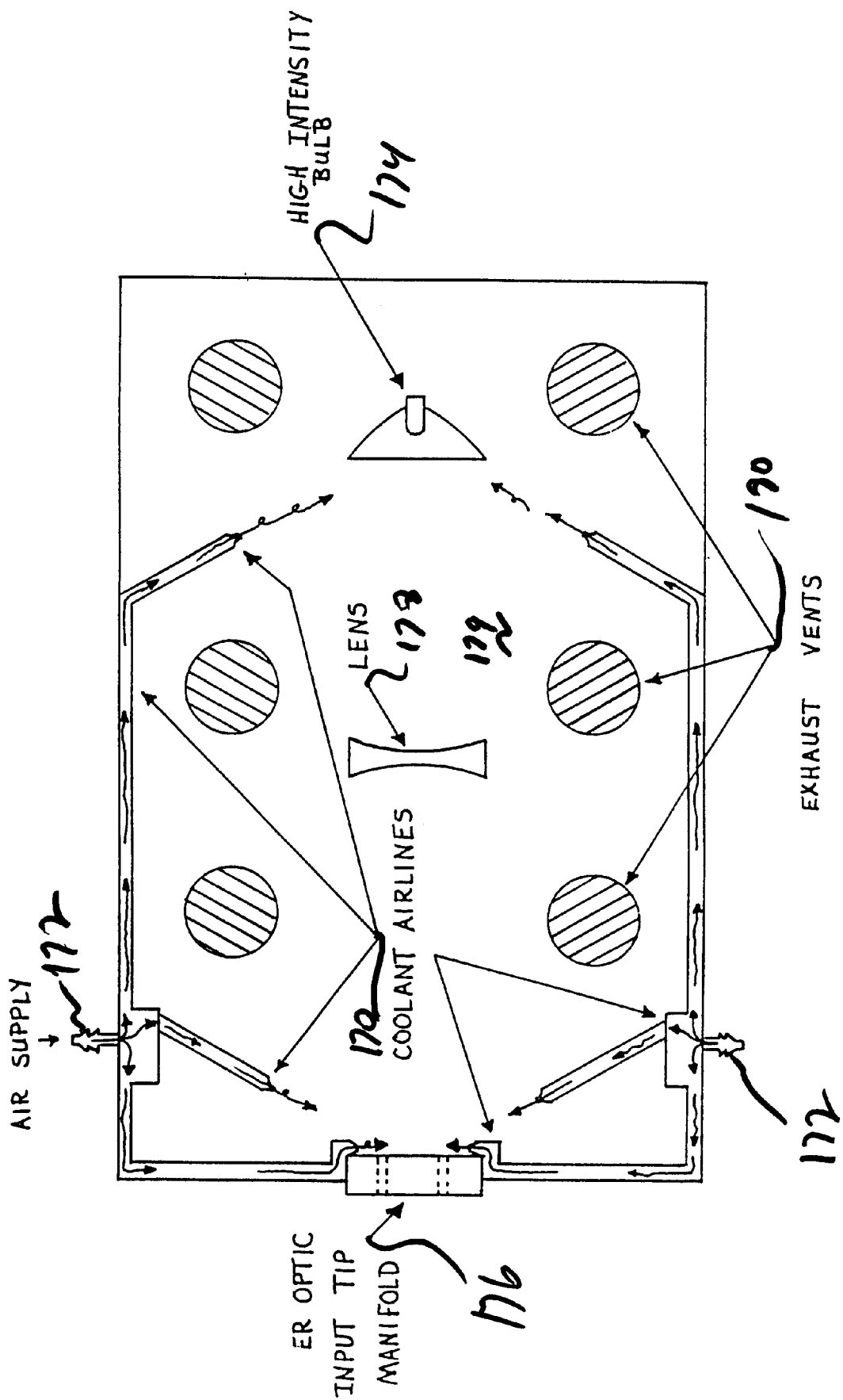

VERSATILE OPERATORY LIGHT SYSTEM

RELATED APPLICATIONS

This application is a Continuation-in-Part of commonly assigned, U.S. Ser. No. 08/401,717 for "VERSATILE OPERATORY LIGHT SYSTEM," filed Mar. 10, 1995 now U.S. Pat. No. 5,775,896.

BACKGROUND OF THE INVENTION

1. Field

This invention pertains to operatory lighting systems, particularly such systems for illuminating the oral cavity of a dental patient. It is particularly directed to a versatile system which provides both hard wired and fiber optic illumination capabilities for dental handpieces.

2. State of the Art

Modern dental offices are conventionally equipped with hand held devices called "handpieces. " A handpiece, most typically an air-driven dental drill, is connected to its drive air supply through a conduit system comprising a portion of a utility bundle. The bundle is usually contained within a long flexible umbilical casing, often called a "hose," or "handpiece tubing," and conventionally includes passageways to accommodate drive air, exhaust air, chip air, water and lighting for the handpiece. U.S. Pat. Nos. 4,334,863; 4,553,938; 4,975,058; 5,088,924 and 5,145,370 describe representative conventional handpiece tubing assemblies of this type.

Lighting has been provided to handpieces by two distinct approaches. According to one approach, a fiber optic bundle is connected at a proximal end to a light generator and at a distal end to a handpiece. The fiber bundle is positioned within the umbilical utility hose (handpiece tubing). The fiber bundles used commercially for this purpose originally comprised glass fibers, although more recently, other light-transmitting fibers, notably acrylic fibers, have been proposed. An alternative arrangement, sometimes called the "power optic" system, positions a high intensity subminiaturized light bulb at the distal end of the umbilical hose. Power is delivered to the bulb through wires strung down the umbilical hose for connection to a power supply. This approach is best illustrated by U.S. Pat. No. 4,334,863.

A major inconvenience in the field has been the incompatibility of components of the fiber optic and power optic systems generally. Fiber optic systems conventionally utilize high intensity "projector" bulbs operated at standard house voltage, e.g. 120 volts. Power optic systems require a low voltage power generator dissimilar from those available in fiber optic systems. Moreover, the power generators furnished by any particular manufacturer have been incompatible with the bulbs associated with the handpiece tubings of the power optic systems supplied by other such manufacturers. Current major suppliers of power optic systems utilize subminiature bulbs which operate at 3.5 volts, 4.09 volts and 5.5–6 volts, respectively. These bulbs each require suitably matched power supplies. Accordingly, once a selected power optic system is acquired, and the appropriate power supply is installed in the field, the purchaser has limited options with respect to replacement parts or upgrades to the system.

Recently, adjustable power supplies for power optic installations have become available. The output voltage of these devices may be adjusted for use with a selected bulb voltage. Once adjusted, however, a single output voltage is available for use. Accordingly, the installation is limited as a practical matter to interfacing with the handpiece tubings of a single selected power optic system. Under current conditions, it remains necessary to provide a plurality of distinct power supplies in association with a dental operatory to support the operation of handpiece tubings furnished by a corresponding plurality of original equipment suppliers.

U.S. Pat. Nos. 4,957,347; 5,052,778 and 5,067,831 together disclose linear optical conduits, and their disclosures are instructive concerning the state of the art with respect to fiber optic technology generally. Among other things, these patents disclose various embodiments of a flexible, clad, monofilament optical conduit constructed around a flexible, light-transmitting, polymeric core characterized by a relatively high refractive index. The core is surrounded by a shrunk, heat shrinkable cladding, which has a relatively low refractive index compared to that of the core. The disclosures of U.S. Pat. Nos. 4,957,347; 5,052,778 and 5,067,831 are incorporated into this disclosure by reference for their teachings of materials and structures which may be incorporated into certain preferred embodiments of this invention.

Typically dental fiber optic handpiece hose assemblies have a smooth-walled aseptic outer tubing that contains a plurality of internal components to provide drive air, an exhaust line, chip air and coolant air to a dental handpiece. Typical dental handpiece bundles use a single airline (drive air) to power an associated handpiece. The drive air line delivers air at positive pressure as it enters a chamber to contact an impeller which drives a turbine, collet and burr. Air continues around the turbine chamber and out the main air exhaust port. The exiting air meets resistance, known as static pressure. Static pressure creates back pressure that retards the turbine assembly from spinning to its full potential.

The fiber optic bundle of a handpiece is typically comprised of stranded glass or acrylic. While either fiber optic bundle allows sufficient light to pass from one end to the other, the characteristically cylindrical strands of such bundles, when packed together, leave voids between the strands. The presence of these voids between the optic fibers results in a failure to utilize all of the available area in the bundle to transmit light.

Certain otherwise suitable light sources have been found to burn out acrylic optic bundles very rapidly; e.g., within 30 seconds from the time the light source is activated. The cause of this rapid destruction has been found to be infra red radiation produced by the light source. These light sources also characteristically produce a heat build-up. Acrylic fibers will burn out or melt down when exposed to minimal amounts of infra red radiation and/or temperatures which exceed 140 degrees Fahrenheit for a duration longer than a few seconds. Acrylic fibers are preferred because of their relatively high light output properties. It has not heretofore been feasible to utilize them in connection with these high intensity light sources.

The coupling of terminal ends of fiber bundles, particularly at plug connections, has been problematic. For example, dental handpiece assemblies typically have a smooth wall aseptic outer tubing that contains a plurality of internal components and lines or tubings in addition to a fiber optic bundle. The output end of the assembly consists of a plastic or metal tube separator with hose barbs, and is shielded with a threaded outer sleeve called a handpiece nut. This nut connects to an optic-containing device. Due to the variety of lengths of the fiber optic pins on the back of the optic-containing device, the fiber optic receptacle in the assembly must be excessively recessed to avoid compression damage. Otherwise, the two juxtaposed, rigidly mounted bundles may be compressed with excessive force, causing damage to the respective optic ends. The recessed receptacle inevitably results in a gap between the optic bundles, thereby effecting a loss in light transmission.

The present invention relates generally to fiber optic light illuminators. Typically, a fiber optic light source consists of a high intensity projector style bulb with a cooling fan. Down sizing a modern light source is restricted by the size of fan needed to cool the bulb. Another disadvantage of the modern day light source is its large size, which requires it to be mounted in a cabinet some distance from chair side. This limitation imposes a length requirement for the fiber optic tubing used to connect a handpiece to the light source. The longer fiber optic tubing adds excessive weight and greater loss of light due to the distance the light must travel from the light source to the handpiece. Low light output and excessive weight are undesirable qualities in fiber optic tubing, as these characteristics cause both eye and hand fatigue to the operator.

SUMMARY OF THE INVENTION

This invention provides a low voltage power supply capable of functioning as the power source for a plurality of handpieces connected through power optic handpiece tubings currently extant in the field. It also provides a unique fiber optic handpiece tubing constructed and arranged to incorporate a subminiature low voltage bulb as the light source; thereby avoiding the need for the conventional high voltage power supply and projector bulb. Individual terminals of the power supply provide regulated voltage at appropriate levels; e.g., 3.5, 4 and 6 volts, to drive, either individually or simultaneously, all of the power optic handpiece tubings currently ubiquitous in the field. The same power supply may be utilized to drive the fiber optic handpiece tubings of this invention.

The novel fiber optic handpiece tubings of this invention preferably comprise a unique acrylic optical bundle. The bundle assembly desirably includes an input tip capable of withstanding the temperatures associated with existing fiber optic light generators and subminiature krypton, halide bulbs; i.e., as high as about 500° F. The acrylic bundle contains fewer strands of larger diameter and is of significantly less weight than conventional glass fiber optic bundles. Its use thus offers the advantages of reduced operator hand fatigue and increased resistance to fiber breakage. Moreover, the acrylic material filters out the undesirable brown, yellow and green portions of the light spectrum passed by typical glass fiber bundles.

The acrylic fiber bundles of this invention may be incorporated into a dental handpiece tubing of the type disclosed by U.S. Pat. Nos. 4,975,058; 5,088,924 and 5,145,370, for example. The input tip can then be associated with a high energy, low voltage, subminiature bulb, connected via a wiring harness to a remote power supply and control circuitry. This capability frees fiber optic operatory lighting from its traditional association with long bundle lengths anchored at one end to a light generator.

The disclosures of U.S. Pat. Nos. 4,334,863; 4,553,938; 4,975,058; 5,088,924 and 5,145,370 are incorporated by reference for their descriptions of handpieces and other components relevant to the systems of this invention. It is contemplated that monofilament optical conduits of the type disclosed by the aforementioned U.S. Pat. Nos. 4,957,347; 5,052,778 and 5,067,831, even if constructed with a core material other than a cured acrylic resinous material, will constitute a highly preferred light conduit for use in the practice of this invention.

As used in this disclosure and the appended claims: the term "high voltage" refers to voltages above about 50 volts, more typically normal house voltages of 120/240 volts nominal; "low voltage" refers to voltages below about 50 volts, more typically below about 10 volts, generally an order of magnitude below "high voltage;" and "subminiature bulbs" refers to incandescent, typically halide or krypton/halide, low voltage bulbs having diameters of less than about ⅛ inch (30 millimeters). While these specific values are not themselves critical, they are currently regarded as embracing the practical range for this invention, and as distinguishing the components of this invention from other devices which would be unsuitable for use within the context of this disclosure. The term "light source" refers generically to bulbs utilized as the source for light delivered by any means through or in connection with a handpiece tubing to a dental handpiece.

The invention may be regarded as comprising various distinct but intercooperable advances in the art; for example: a novel, low voltage fiber optic handpiece tubing arrangement, and a specialized multi-output, variable low voltage power supply capable of powering multiple subminiature bulbs. Other advances capable of incorporation into the handpiece tubing arrangements of this invention include specialized venturi effect air lines, polymer optical fibers, infra red blockers, spring-loaded input tips and light source cooling systems, A notable component of the preferred embodiments of this invention is a novel system for conducting light to a dental handpiece. The system comprises a bundle of flexible, light-conducting fibers directly associated with a subminiature bulb. The bundle has a first end structured to terminate in a window capable of receiving light from the bulb, and a second end capable of emitting light conducted by the bundle from its first end. A first coupling fixture associated with the first end of the bundle is structured and arranged to hold a subminiature bulb within the fixture juxtaposed with respect to the window when the first end of the bundle is inserted within the first coupling. A second coupling fixture is associated with the second end of the bundle, and is structurally adapted for connection to a dental handpiece. When so attached, illumination is furnished through the handpiece in generally conventional fashion. Of course, the bundle generally comprises a handpiece tubing arrangement.

The first coupling fixture ideally includes a heat-conducting body with a longitudinal axis and a first longitudinal passage approximately parallel that axis. This first longitudinal passage will have a proximal end, closest to the power source, and a distal end, closest to the fiber bundle. The proximal end is structurally configured to receive and contain a subminiature bulb. The distal end is structurally configured to receive the first end of the bundle. A heat-insulating, light-transmitting plug, such as a length of glass rod, may be positioned within the first longitudinal passage to occupy a portion of that passage between a bulb-receiving portion of the proximal end of the passage and a bundle-receiving portion of the distal end of the passage. Other embodiments include a second longitudinal passage through the heat-conducting body, approximately parallel the first longitudinal passage. The second longitudinal passage is provided with barbed fixtures at an inlet end and an outlet end to accommodate the flow of cooling fluid, typically air, through the second longitudinal passage. The complete system includes a low voltage power supply connected to power a subminiature bulb associated with the first coupling fixture.

A power supply of this invention includes a plurality of output terminal pairs electrically connected to a power source through circuitry constructed and arranged to permit individual adjustment of the voltage applied between the terminals of each such pair. The circuit constitutes means for powering simultaneously a plurality of light sources at individually selected voltages. A useful such power supply generally includes a housing; a plurality of output terminal pairs mounted to the housing; a power source associated with the housing; and electrical circuitry interconnecting the terminal pairs with the power source. The circuitry is constructed and arranged to permit individual adjustment of the voltage applied between the terminals of each terminal pair. In this fashion, the power supply is enabled to provide power simultaneously to a plurality of light sources at individually selected voltages. The power supply may be installed in combination with a plurality of dental handpiece tubings, each such tubing carrying a low voltage light source, and each such light source being connected to a selected terminal pair.

Certain embodiments of the invention include an additional source of air from the existing main air line or a separate air line within a bundle, an extruded bundle or in the device itself (i.e., dental handpiece) through a "Y" connection into the main air exhaust, creating a venturi. This venturi effect significantly reduces any back pressure in the turbine chamber. Diameters and PSI flow rates can be less than, greater than or equal to each other for air and exhaust lines. The exhaust air line can be open or it can direct exhaust air to auxiliary apparatus adapted to capture oil or debris. This apparatus may include a capture vessel containing a filter to allow pressure escape. The filter will preferably be constructed to prevent back pressure—either air or water. The venturi line of this invention can be adapted to a variety of applications in the dental, medical, surgical and industrial fields. Various applications may require or include an orifice, whose diameter, length or configuration can be selected according to known principles as required by the application. Similarly, various combinations of tubing sizes or lengths can be selected to achieve optimum performance.

The present invention provides an improved polymer optical fiber with increased light-transmitting capacity. Modern advancements enable the extrusion of synthetic material, such as plastics, organic polymers, acrylics or silicones, into an outer sheathing. This invention extrudes a solid core of light-transmitting material into a thin-walled tube of heat and chemical resistant material, notably Teflon™, to create a solid core optic bundle. The core may be air-, fluid- or gas-filled to effect a semi-solid character. In any case, the optic bundle yields much higher output than can be delivered by means of multi strand glass or acrylic bundles. The lighting core may be illuminated through either or both end or linear lamination arrangements. Moreover, the core may be provided in various diameters, depending upon the requirements of a particular application. The preferred embodiment utilizes a solid core, organic polymer which is end-light in nature. A material selected from the Lumenyte™ Stayflex™ Solid Core Series is currently preferred. This solid core material utilizes more of the area available for light transmission which minimizes light loss. A Teflon™ or Flexcoat™ cladding provides ultraviolet, algicide and funicide inhibitors.

Preferred embodiments of this invention position a length of synthetic or organic polymer optical fiber, such as Lumenyte's SL™, EL™ or Stayflex™ solid core or non-solid (air, fluid or gas filled) core acrylic or other plastic optic light transmitter between an acrylic fiber optic bundle and a high intensity light source. This "infra red blocker" segment provides a solution to both the infra red burnout as well as the thermal damage experienced when acrylic fibers are exposed to infra red and high heat. Preferred embodiments utilize point lighting, although linear lighting is within contemplation. Cladding may optionally be provided for the "infra red blocker" segment. The currently preferred cladding materials include Teflon™ or a Flexcoat™ sheaths, which provide ultraviolet, algicide and fungicide inhibitors. The Lumenyte product line is well-suited to this application as these optic light transmitters are more resistant to infra red damage and are capable of operating in a wide range of temperatures (from a negative four degrees to an excess of 260–275 degrees Fahrenheit) for extended periods of time without sustaining any notable damage.

As a precautionary measure for infra red sensitivity, an infra red blocker may be included within a light transmission system Various expedients may be incorporated to accomplish infra red blocking, whereby to protect both of a pair of optic transmitters while they are coupled together and in operation. A dichroic vapor coating (or equivalent)is effective for this purpose. A lens may also be applied either mechanically (by swaging) or chemically (using an adhesive). Among possible arrangements, are:

A. A length of Stayflex™ organic polymer fiber may be used in conjunction with or without a glass rod. The fiber may be suitable by itself or it may be used in conjunction with an additional blocker; e.g., a coating or a lens. The coating or lens may be placed on the input or output side of the glass rod or the Stayflex™ material, in the light source between the bulb and lens, between the lens and bundle or any combination of such locations.

B. A glass rod may be used as the input tip, coupled directly to the acrylic fibers. It may be used by itself or with a coating or lens. The coating or lens may be placed on the input or output side of the glass rod, in the light source between the bulb and lens, between lens and bundle or any combination of such locations C. A coating or lens may be applied directly to the acrylic fiber. The coating or lens may be placed on the input side of the acrylic fiber, in the light source between the bulb and lens, between the lens and bundle or any combination of such locations.

Certain embodiments of the present invention incorporate a spring and sliding sleeve in association with the fiber optic output tip, thereby enabling the optic bundle in a fiber optic bundle assembly to move back and forth freely. This arrangement enables the fiber optic terminal plug on the back of an optic device (such as a dental handpiece) and the fiber optic bundle in a handpiece nut to contact each other at all times without concern of damage to the optics due to over-tightening. This improvement substantially increases light output by eliminating the void between the two terminal ends so that degradation of the transmission of light by gaps at the junction between bundles is avoided. Devices which benefit from this improvement include medical and dental devices which contain fiber optic light and industrial applications which require fiber optic lighting. The list of devices include but are not limited to high and low speed handpieces, lighted mirrors, lighted hand instruments, ultrasonic scalers, intra-oral cameras, medical cutting tools, industrial grade cutting and tuning instruments.

The present invention further provides an improved cooling system which relies upon a cooling chamber, rather than a cooling fan. The chamber houses the bulb and bundle input tip. The invention can be adapted to metal halide, quartz halogen, xenon metal or halide lamps as well as to miniature style bulbs. A miniature cooling chamber may be provided around a high intensity bulb. Alternatively, a means for cooling the light source may comprise a series of cooling ports. The cooling ports can be directed at the bulb, at input tips either inside or outside the light source or through the fiber optic holes where the input tips enter the light source. Two tubes of equal lengths but different diameters are arranged concentrically. These tubes define an annular air space between the two tubes, and a ring is positioned in the back end to seal the cooling chamber. The front of the chamber is sealed by a solid plate, which is structured and arranged to enable the insertion of fiber optic input tips through one or more small holes. The cooling chamber has a hose barb at each end to allow a continuous flow of coolant air. A high intensity bulb is located inside the smaller tube of double-walled air-cooled chamber to illuminate fiber optic bundle(s) at the front section of that chamber.

While it is proposed to use an existing air line which powers the turbine in a handpiece, the invention is not restricted to using the existing main air line. Cooling sources could come from an independent line and may include alternative cooling methods, such as internal or external air ports in front of or behind bulb, across the input tips at either one of or both sides of the fiber receptacle or any combination of such expedients. Cooling may be accomplished with various mediums, including air or water. Yet another means of cooling the input tip is be to provide a channel(s) through the fiber receptacle to the input holes. Cooling in this fashion may be provided by retrofitting all existing light sources. The cooling chamber can be constructed from synthetic or metallic material.

Another advantage of the cooling chamber is that the reduction of the overall size of the fiber optic light source enables the unit to be located at or near the point of use or the patient's chair side. This placement allows for a shorter fiber optic tubing resulting in brighter fiber optic outputs and less weight to maneuver by the operator.

BRIEF DESCRIPTION OF THE DRAWINGS

In the drawings, which illustrate what is currently regarded as the best mode for carrying out the invention.

FIG. 4 is an enlarged fragment of the assembly of FIG. 3, taken from the region 4—4 of FIG.3;

FIG. 5 is a view in elevation, taken from the reference line 5—5 of FIG. 3;

FIG. 6 is a view in cross section, taken along the reference line 6—6 of FIG. 3;

FIG. 7 is a pictorial view, partially in section, of a preferred optical coupler of this invention;

FIG. 10 is a perspective view of a venturi line embodiment of this invention;

FIG. 11 is a perspective view of a Lumenyte optical fiber component of this invention;

FIG. 12 is fragmentary view in elevation of a light pipe assembly, including the optical fiber of FIG. 11;

FIG. 15 is a view in elevation of a light source cooling system;

FIG. 16 is a view in elevation of the input end of the cooling system of FIG. 15;

FIG. 17 is a view in elevation of the outlet end of the cooling system of FIG. 15; and FIG. 18 is a plan view of the cooling system of FIG. 15.

DESCRIPTION OF THE ILLUSTRATED EMBODIMENTS

Figure 1:
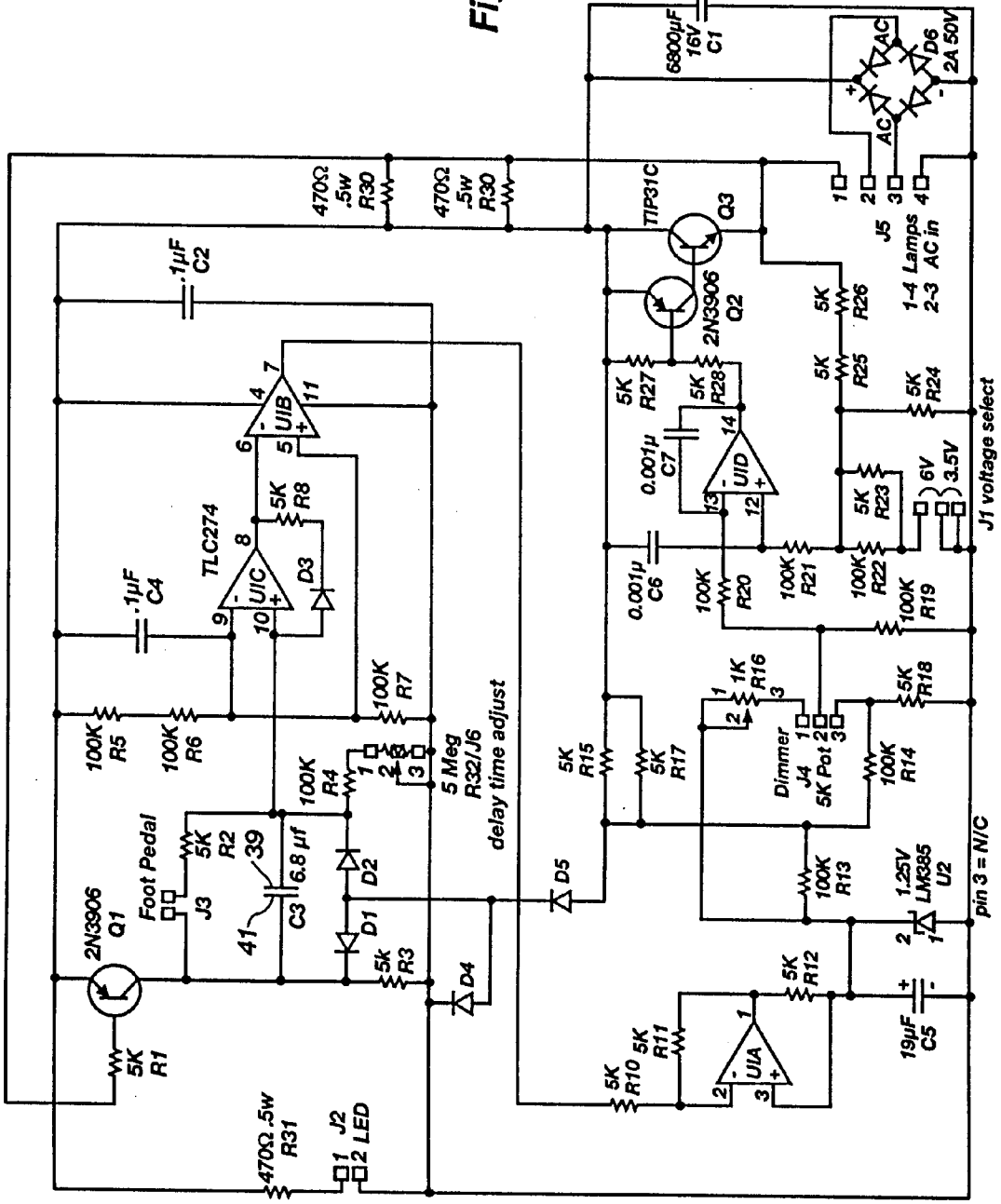
FIG. 1 is a schematic diagram of a simple version of the power supply of this invention.
Figure 2:
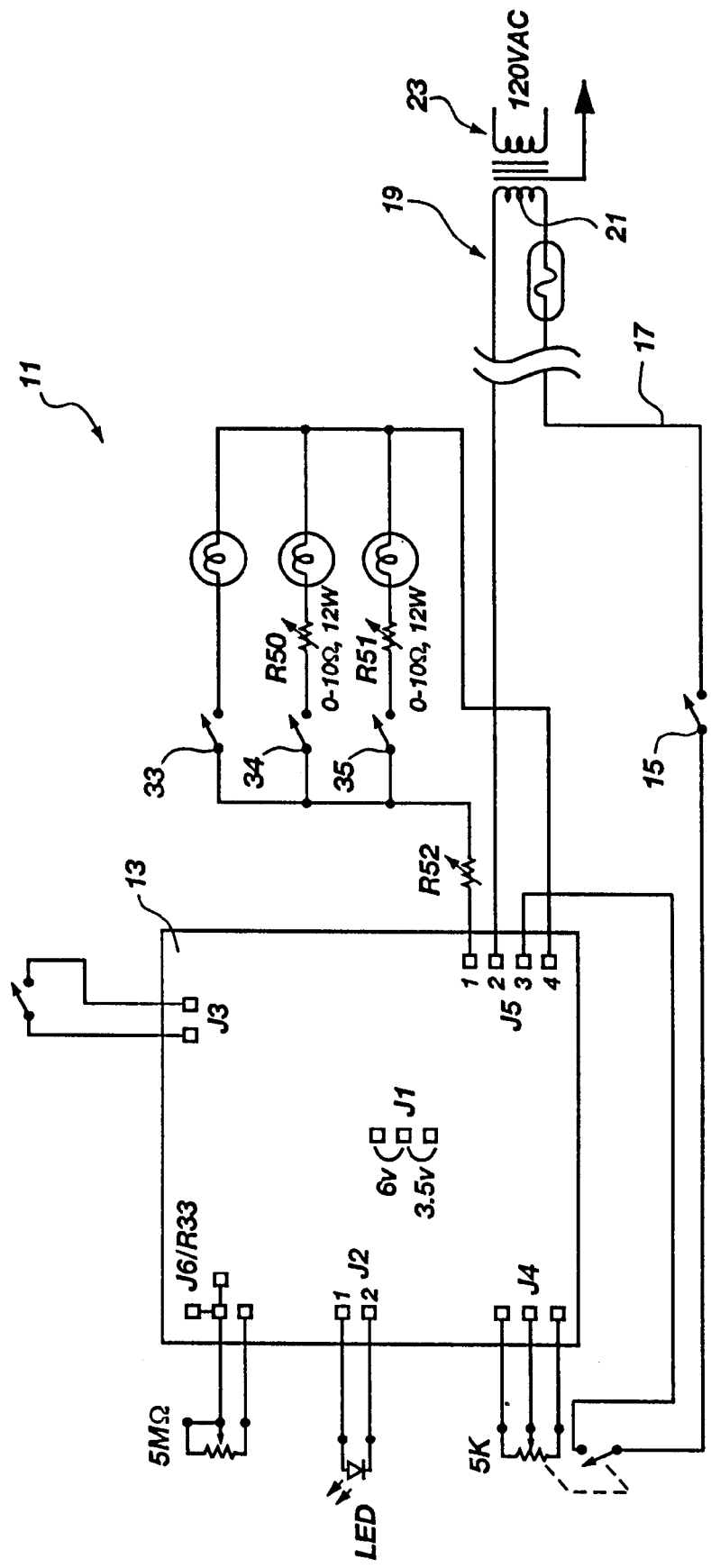
FIG. 2 is a schematic diagram of a system incorporating the power supply of FIG. 1.
Figure 9:
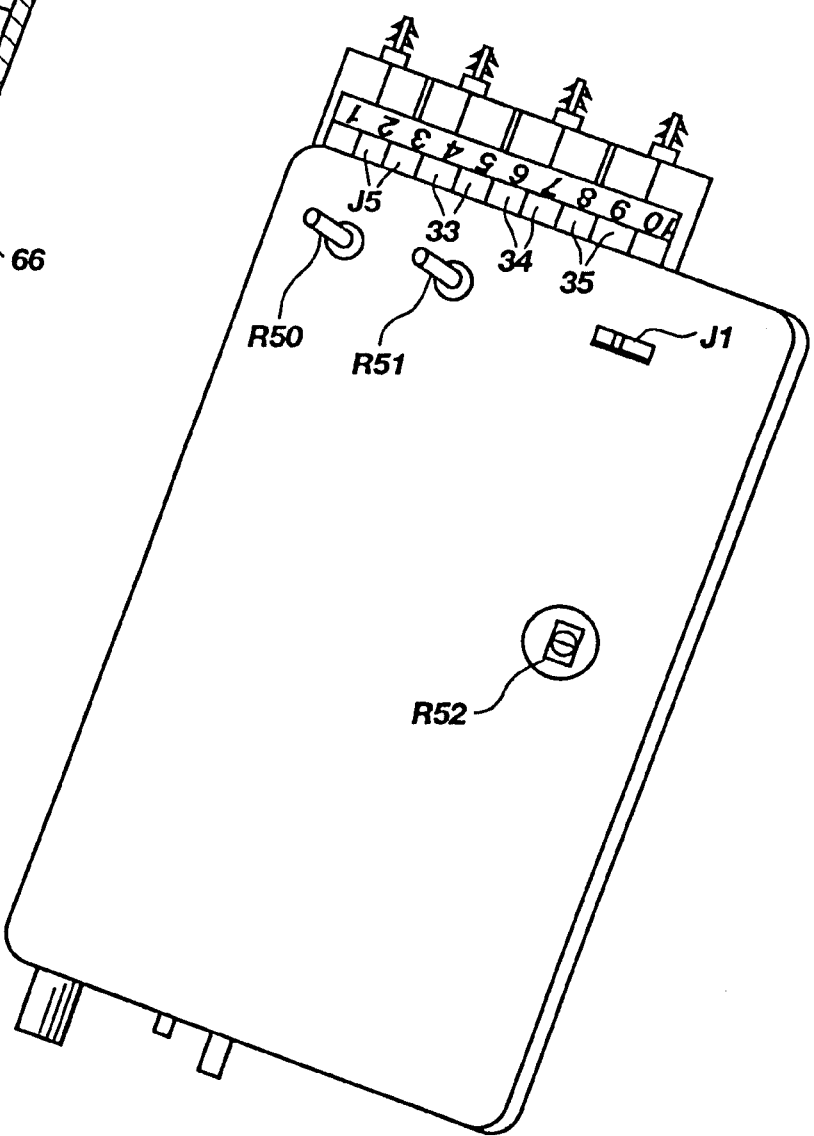
FIG. 9 is a pictorial view of an assembled power supply of this invention.

As illustrated by FIGS. 1, 2 and 9, a light controller, generally 11, includes a circuit board 13 associated with voltage selection terminals, J1, LED display, J2, a foot pedal air switch, J3, a dimmer control, J4, handpiece holder switch circuits, J5, an optional time adjustment, J6, and a master air switch 15 in the fused conductor 17 of a power cord 19 leading from the low voltage side 21 of a power transformer 23.

Practical components of the circuit board 13 are shown by FIG. 1, 3.5 or 6 volt DC power is selected at J1, and is supplied to 720 ma incandescent lamps at J5. The timer at J6 turns on for an adjustable 1–35 second period when a handpiece is removed from a holder to activate a switch 33, 34, 35 (FIG. 2) at J5. The timer remains on for so long as the foot switch at J3 is closed and remains on for a delay of 1–35 seconds after the switch is again opened. With a handpiece out of its holder, a quiescent voltage (typically 5–10% of its normal operating voltage) is applied across the lamp to enhance its useful life. An approximately 1.5 volt reference drop across diodes D4 and D5 is fed across the resistors R13 and R14 to provide this bias voltage. The illustrated circuit also functions through operational amplifier U1A and capacitor C5 to increase the applied voltage gradually over a fraction (typically 0.3) of a second when a lamp is energized.

Power is applied to pins 2 and 3 of J5 at about 5 or 7 volts AC. It is rectified by the diode bridge D6 and filtered by capacitor Cl. Operational amplifier U1D and transistors Q2 and Q3 comprise a regulator for the incoming voltage to insure application of the proper lamp voltages at J1. Reference diode U2 provides, through the dimmer potentiometer R16, a reference voltage for the regulator. The lamp voltage is thus maintained at 3 or 5.13 times the voltage detected at pin 2 at J4. R16 may be adjusted to effect a maximum dimmer output of 1.167 volts, thereby setting the maximum J1 terminal voltages at 3.5 and 6 volts, respectively.

Operational amplifier U1B inverts the on/off signal from the timer output at J6. Operational amplifier U1C functions as a comparator for the timer circuit. When a lamp is on, both sides of the timer capacitor C3 are at high potential. As the capacitor C3 charges through timing resistors R4 and R32, the potential at one side 39 of the capacitor C3 falls below the level set by resistors R5, R6 and R7. The output of amplifier U1C then becomes low, causing a high output from amplifier U1B, shutting off the bias current to diode U2. The output potential at J1 then shuts off, except for the quiescent voltage across resistors R13 and R14.

When all handpieces are in their holders, there is no load across the regulator output. This output thus floats up to match the incoming supply voltage, thereby turning off transistor Q1. The potential on the side 41 of capacitor C3 then reduces. Diode D2 prevents the potential applied to the side 39 of capacitor C3 from reducing to below the negative supply voltage. When a handpiece is removed from a holder, the regulator output voltage returns to its quiescent level, thereby turning on transistor Q1 to raise the potential at 41. Because the capacitor C3 is discharged, the potential at 39 also increases, turning on the reference voltage biases to the operational amplifiers U1A, U1B and U1C.

If it is desired to operate only 3.5 volt bulbs, the appropriate selection is made at J1 at the time the power supply is installed. The voltage applied between pins 1 and 4 of J5 is then 3.5 volts. Power resistors R50 and R51 remain set at approximately zero ohms resistance, and the voltage applied at each of the lamp switches 33, 34 and 35 remains at 3.5 volts. The voltage at each of these switches may be adjusted to 6 volts at J1. Assuming that the voltage selected at J1 is 6 volts, the voltage applied at each of the switches 33, 34 and 35 my be adjusted to a lesser common voltage, e.g. 4 volts, by adjustment of variable resistor R52. Power resistors R50 and R51 may be individually adjusted to provide reduced voltages at switches 34 and 35. It is thus possible to provide power for three different handpiece tubing assemblies, each operating at any selected voltage up to about 6 volts. In the event it becomes desirable to provide different handpiece tubings at the operatory subsequent to the initial installation, the existing power supply can be adjusted in the field, rather than replaced.

The illustrated power supply is suitable for operation of the fiber optic handpiece tubing of this invention through any of the switches 33, 34 and 35 adjusted to provide appropriate output voltage. The bulbs currently preferred for the illustrated embodiments have a focal point of approximately ¹⁄₁₀ inch, and require approximately 6 volts for optimum operation.

Figure 8:
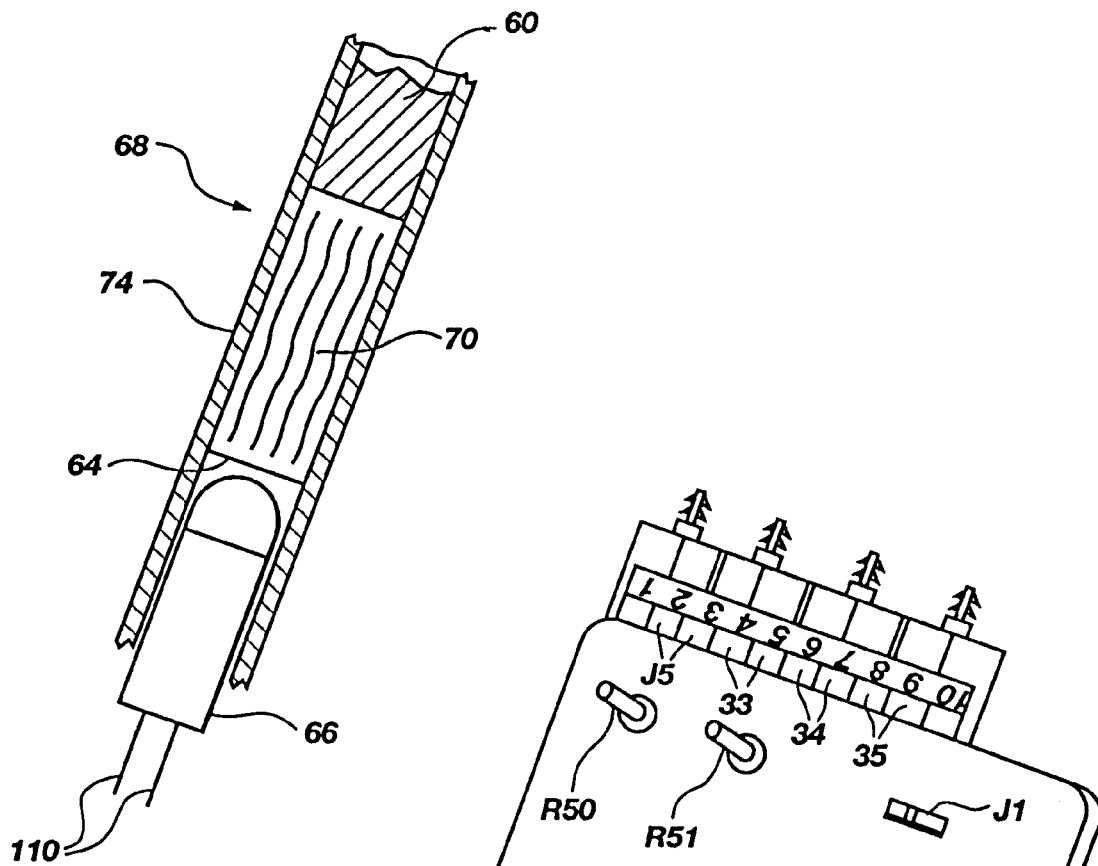
FIG. 8 is a view in section of an alternative optical coupler of this invention.

A preferred fiber optic assembly of this invention is best shown by FIGS. 3–6, while its manner of coupling to a low voltage light source is illustrated by FIGS. 7 and 8. The bundle, generally 60, illustrated is an acrylic bundle of the type disclosed in U.S. Pat. Nos. 4,975,058; 5,088,924 and 5,145,370, and may be provided in any convenient length, typical standard lengths being between about 6 and about 14 feet. Acrylic bundles comprising between 1 and 64 fibers are currently regarded as useful for this invention. The diameters of the individual fibers in a bundle will be dependant upon their total number and the diameter of the bundle. An exemplary bundle 60 incorporates 19 strands of 0.020 inch diameter acrylic fibers bonded within an end fitting 62 with clear R.T.V. resin. A more flexible bundle utilizes a greater number of smaller diameter fibers. The terminus 64 of the fitting is polished to constitute an entry window to receive light from a bulb 66 (FIGS. 7 and 8). The optical coupler 68 positions a short, typically about 1 to about 2 inches of a clear insulating material, typically glass rod 70, between the bulb 66 and the fiber bundle 60. The glass rod illustrated is capable of withstanding temperatures as high as 500° F. These components are contained within a heat conductive casing, such as the aluminum block 74 shown. FIG. 7 illustrates a coupling arrangement which provides for cooling air circulating through a passage in the aluminum block 74 between first 78 and second 80 tubing connectors. Either connector, 78, 80, may function as the air inlet, depending upon whether drive or exhaust air is circulated through the block 74. In the embodiments illustrated by either of FIG. 7 or 8, the insulating rod 70 may be fixed in place, thereby avoiding the need to fabricate fiber bundles which individually incorporate these components.

A conventional grooved proto tip 86 (FIG. 3) at the output end 88 of the bundle 60 connects to a handpiece in conventional fashion. Referring to FIGS. 4–6, the fibers 92 of the bundle 60 are positioned within a siliconized polyurethane sheathing 94, which is fastened to a rod holder 96 swaged to a clad rod end tip 98. A length 100 of shrink tubing protects the source end 104 of the bundle 60 from damage which could result from severe bending.

Figure 3:
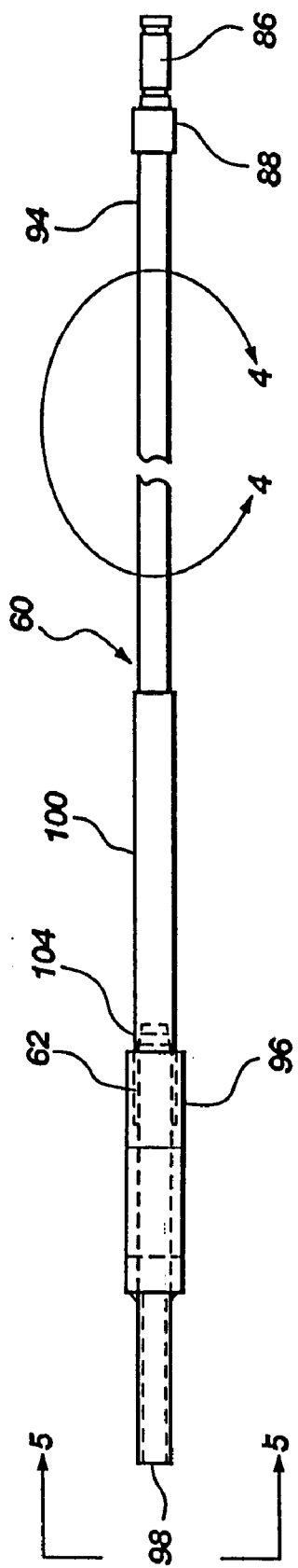
FIG. 3 is a pictorial view of a fiber optic bundle assembly of this invention.

It should be recognized that the optical bundle illustrated by FIG. 3 may be appreciably shorter that the handpiece tubing within which it is contained. The wires 110 illustrated in FIGS. 7 and 8 may be of any convenient length, and the optical couplers 68 may be located at any desired position between the power supply 11 and output end 88 of the bundle 60.

FIG. 10 illustrates a supply hose, generally 95, with a plurality of supply lines, generally 96 within a sheath 97. Included within the sheath 97 are a main air line in 98 and an exhaust air line 99. An independent venturi tube air line 100 connects through a "Y" adaptor 101 to the exhaust line 99.

Figure 13:
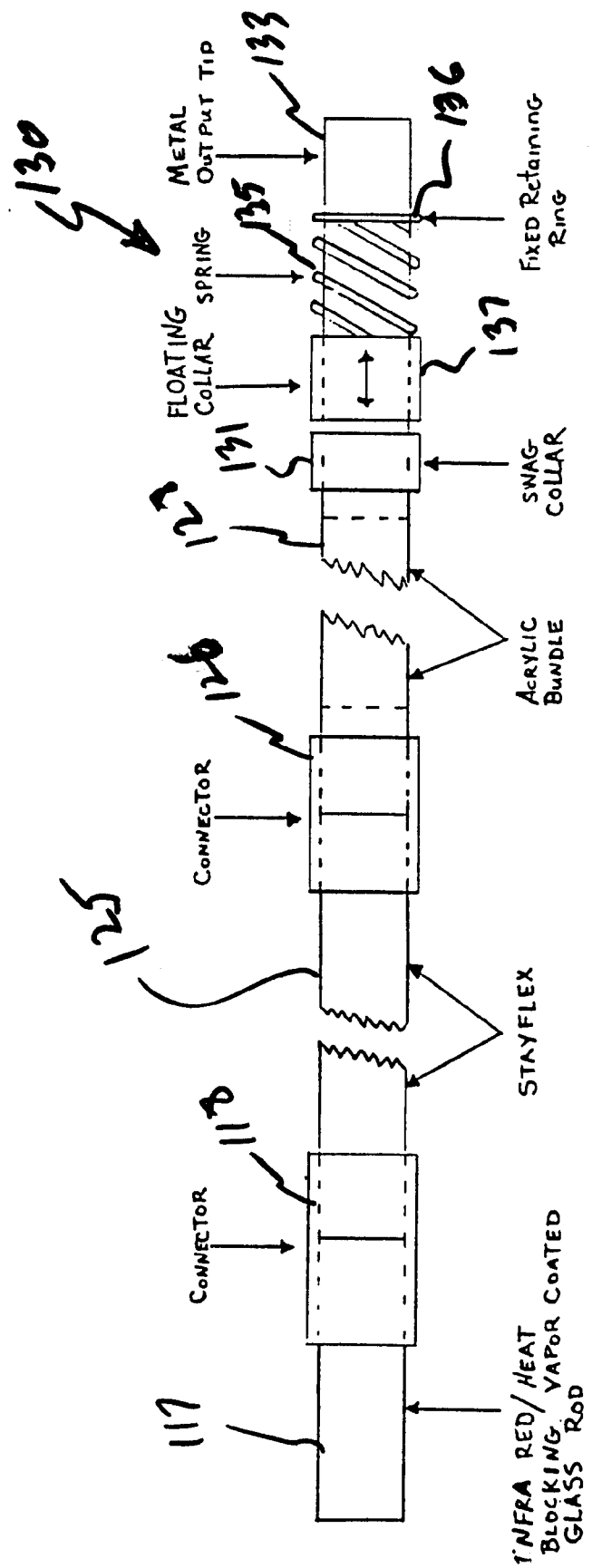
FIG. 13 is a fragmentary view of an alternative light pipe embodiment incorporating an infra red blocker.
Figure 14:
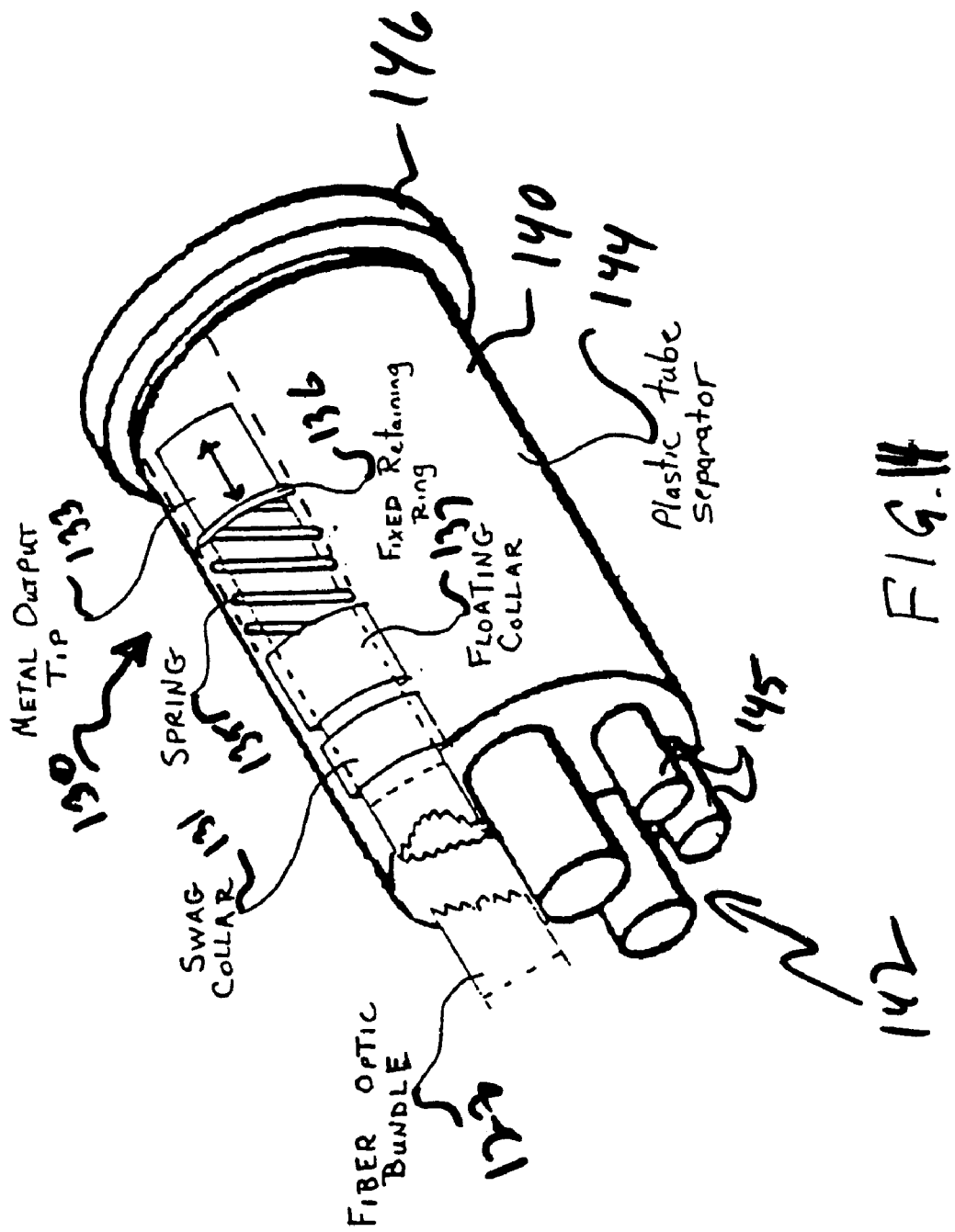
FIG. 14 is a perspective view of a spring-loaded input tip.

FIGS. 11 and 12 illustrate a Lumenyte STA-FLEX™ LEF linear light-emitting optical fiber 110, including a light-transmitting core 111, a fluoropolymer cladding 112 and a black bondable jacket 113, The core 111 is extruded into the cladding 112. A stainless steel output tip 115 is attached to the bundle 110 by means of a swaged collar 116. An infra red/heat blocking, vapor coated glass rod 117 is attached at the opposite end of the fiber 110 by means of a connector 118. FIG. 13 illustrates a similar arrangement with additional features. A STA-FLEX™ segment 125 is interposed, through connectors 118, 126 between the glass rod 117 and an acrylic fiber bundle 128. An output tip assembly, generally 130, includes a swaged collar 131, connecting a metal tip 133 to the bundle 128. A spring 135 is carried by the tip 133 between a fixed ring 136 and floating collar 137. FIG. 14 illustrates the tip assembly 130 of FIG. 13 in mounted association with an input tip 140 of a dental handpiece (partially shown). The input tip 140 includes utility lines, generally 142, within a plastic tube separator 144 with hose barbs 145 and a handpiece nut 146.

FIGS. 15–17 illustrate a light source cooling system, generally 150, which circulates air within an annular chamber 152 defmed by concentric tubes 153, 154. A high intensity bulb 156 is mounted within the lumen 157. A coated lens 158 is similarly installed between the bulb 156 and an end plate 159, which is provided with input tip receptacle holes 160 and cooling ports 161. Inlet 163 and outlet 164 hose barbs are provided for air supply and control. FIG. 18 illustrates an alternative arrangement in which air lines 170 receive coolant air from inlets 172. Air is directed towards a light source 174 and a fiber optic input tip manifold 176, which, together with a lens 178, are installed within a chamber 179. Air is exhausted through vents 180.

Reference to specific details of the illustrated embodiments is not intended to restrict the scope of the appended claims. These claims recite those details regarded as significant to the invention, and are intended to include within their scope all equivalents adduceable by one skilled in the art from this disclosure.

What is claimed is:

1. A system for conducting light to a handpiece, said system comprising:

a light-conducting core extruded into a tubular sheath to form a light-transmitting bundle, said bundle having a first end structured to terminate in a window capable of receiving light from a light source and a second end capable of emitting light conducted by said bundle from said first end;

a first coupling fixture associated with said first end structured and arranged to interface with a light source; and a second coupling fixture associated with said second end and structurally adapted for connection to a handpiece, whereby to furnish illumination through said handpiece.

2. A system according to claim 1, wherein said bundle comprises a handpiece tubing arrangement.

3. A system according to claim 1, wherein said first coupling fixture includes a heat-conducting body with a longitudinal axis and a first longitudinal passage approximately parallel said axis, said first longitudinal passage having a proximal end and a distal end, said proximal end being structurally configured to receive and contain a subminiature bulb and said distal end being structurally configured to receive said first end of said bundle.

4. A system according to claim 3, including a heat-insulating, light-transmitting plug within said first longitudinal passage, occupying a portion of said first longitudinal passage between a bulb-receiving portion of said proximal end and a bundle-receiving portion of said distal end.

5. A system according to claim 3, including a second longitudinal passage through said body, approximately parallel said first longitudinal passage, said second longitudinal passage having an inlet end and an outlet end, whereby to accommodate the flow of cooling fluid through said second longitudinal passage.

6. A system according to claim 1, including a low voltage power supply connected to power a subminiature bulb associated with said first coupling fixture.

7. A system according to claim 6, wherein said first coupling fixture includes a heat-conducting body with a longitudinal axis and a first longitudinal passage approximately parallel said axis, said first longitudinal passage having a proximal end and a distal end, said proximal end being structurally configured to receive and contain said subminiature bulb and said distal end being structurally configured to receive said first end of said bundle.

8. A system according to claim 6, wherein said power supply includes a plurality of output terminal pairs electrically connected to a power source through circuitry constructed and arranged to permit individual adjustment of the voltage applied between the terminals of each said pair, whereby to provide means for powering simultaneously a plurality of light sources at individually selected voltages.

9. A system for conducting light to an optic device, said system comprising:

a bundle of flexible, light-conducting fibers, said bundle having a first end structured to terminate in a window capable of receiving light from a light source and a second end capable of emitting light conducted by said bundle from said first end;

a first coupling fixture associated with said first end, structured and arranged to hold said window in association with a light source;

a second coupling fixture associated with said second end and structurally adapted for connection to a receptacle carried by said optic device, said second coupling fixture comprising a spring biased terminal end segment of said bundle including said second end.

10. A system according to claim 9, wherein said bundle comprises a handpiece tubing arrangement.

11. A system according to claim 9, wherein said first coupling fixture includes a heat-conducting body with a longitudinal axis and a first longitudinal passage approximately parallel said axis, said first longitudinal passage having a proximal end and a distal end, said proximal end being structurally configured to receive and contain a subminiature bulb and said distal end being structurally configured to receive said first end of said bundle.

12. A system according to claim 11, including a heat-insulating, light-transmitting plug within said first longitudinal passage, occupying a portion of said first longitudinal passage between a bulb-receiving portion of said proximal end and a bundle-receiving portion of said distal end.

13. A system according to claim 11, including a second longitudinal passage through said body, approximately parallel said first longitudinal passage, said second longitudinal passage having an inlet end and an outlet end, whereby to accommodate the flow of cooling fluid through said second longitudinal passage.

14. A system according to claim 9, including a low voltage power supply connected to power a subminiature bulb associated with said first coupling fixture.

15. A system according to claim 14, wherein said first coupling fixture includes a heat-conducting body with a longitudinal axis and a first longitudinal passage approximately parallel said axis, said first longitudinal passage having a proximal end and a distal end, said proximal end being structurally configured to receive and contain said subminiature bulb and said distal end being structurally configured to receive said first end of said bundle.

16. A system according to claim 14, wherein said power supply includes a plurality of output terminal pairs electrically connected to a power source through circuitry constructed and arranged to permit individual adjustment of the voltage applied between the terminals of each said pair, whereby to provide means for powering simultaneously a plurality of light sources at individually selected voltages.

17. A system for conducting light to an optic device, said system comprising:

a bundle of one or more flexible, light-conducting fibers, said bundle having a first end structured to terminate in a window capable of receiving light from a light source and a second end capable of emitting light conducted by said bundle from said first end;

a first coupling fixture associated with said first end, structured and arranged to hold said window in association with a light source;

a second coupling fixture associated with said second end and structurally adapted for connection to an optic device; and Infra red blocking means interposed between said first and second coupling fixtures.

* * * * *